United States Patent
Kawasaki et al.

[11] Patent Number: 5,981,423
[45] Date of Patent: Nov. 9, 1999

[54] PROCESS FOR PREPARING VULCANIZATION PROMOTER FOR FLUORINE-CONTAINING ELASTOMERS

[75] Inventors: Hiroshi Kawasaki; Akihiro Naraki; Haruyoshi Tatsu, all of Kitaibaraki, Japan

[73] Assignee: Nippon Mektron, Limited, Tokyo, Japan

[21] Appl. No.: 09/150,782

[22] Filed: Sep. 10, 1998

[30] Foreign Application Priority Data

Nov. 14, 1997 [JP] Japan .................................. 9-331036

[51] Int. Cl.$^6$ ........................................ B01J 31/18
[52] U.S. Cl. ........................ 502/164; 502/150; 502/151; 502/162; 502/172
[58] Field of Search .................... 502/150, 151, 502/162, 164, 172

[56] References Cited

U.S. PATENT DOCUMENTS

| | | | |
|---|---|---|---|
| 4,831,083 | 5/1989 | Geri et al. | 525/199 |
| 4,912,171 | 3/1990 | Grootaert et al. | 525/340 |
| 5,086,123 | 2/1992 | Guenthner et al. | 525/276 |
| 5,177,148 | 1/1993 | Arcella et al. | 525/133 |

FOREIGN PATENT DOCUMENTS

B2-59-23577  6/1984  Japan .

*Primary Examiner*—Elizabeth Wood
*Attorney, Agent, or Firm*—Barnes & Thornburg

[57] ABSTRACT

A vulcanization promoter for fluorine-containing elastomers prepared by (1) allowing 1.01 to 1.15 moles of a quaternary phosphonium salt to react with one mole of monoalkali metal salt of bisphenol AF in alcohol, (2) allowing 2.02 to 2.30 moles of a quaternary phosphonium salt to react with one mole of a dialkali metal salt of bisphenol AF in alcohol, (3) allowing one mole each of an alkali metal alkoxide and bisphenol AF to react with 1.01 to 1.15 moles of a quaternary phosphonium salt in alcohol or (4) subjecting one mole of bisphenol AF, 1.01 to 1.15 moles of a quaternary phosphonium salt and one mole of an alkali metal alkoxide to reaction in alcohol, each followed by further addition of the bisphenol AF thereto, or (5) allowing 1.01 to 1.15 moles of a quaternary phosphonium salt to react with one of ¼alkali metal salt of bisphenol AF in alcohol gives much more improved vulcanization characteristics such as vulcanization speed, etc. while maintaining advantageous properties such as distinguished normal state physical properties as observed in case of vulcanization promoters of bisphenol AF-quaternary phosphonium salt series.

9 Claims, No Drawings

PROCESS FOR PREPARING VULCANIZATION PROMOTER FOR FLUORINE-CONTAINING ELASTOMERS

BACKGROUND OF THE INVENTION

1. Field of the Invention

The present invention relates to a process for preparing a vulcanization promoter for fluorine-containing elastomers and more particularly to a process for preparing a vulcanization promoter of bisphenol AF/quaternary phosphonium salt series for fluorine-containing elastomers.

2. Description of Related Art

JP-B-59-23577 discloses improvement of 100% modulus, stress at break, etc. of vulcanization products by further adding an equimolar compounds of bisphenol AF/quaternary phosphonium salt to a composition comprising a fluorine-containing elastomer, a divalent metal oxide or hydroxide and bisphenol AF.

SUMMARY OF THE INVENTION

An object of the present invention is to provide a process for preparing a vulcanization promoter for fluorine-containing elastomers, which gives much more improved vulcanization characteristics such as vulcanization speed, etc., while maintaining advantageous properties such as distinguished normal state physical properties as observed in case of vulcanization promoters of bisphenol AF/quaternary phosphonium salt series.

The object of the present invention can be attained by preparing a vulcanization promoter for fluorine-containing elastomers either according to a process comprising (1) allowing 1.01 to 1.15 moles of a quaternary phosphonium salt to react with one mole of monoalkali metal salt of bisphenol AF in alcohol, (2) allowing 2.02 to 2.30 moles of a quaternary phosphonium salt to react with one mole of dialkali metal salt of bisphenol AF in alcohol, (3) allowing one mole each of an alkali metal alkoxide and bisphenol AF successively to react with 1.01 to 1.15 moles of a quaternary phosphonium salt in alcohol, or (4) subjecting one mole of bisphenol AF, 1.01 to 1.15 moles of a quaternary phosphonium salt and one mole of an alkali metal alkoxide to reaction in alcohol, each followed by further addition the bisphenol AF thereto and followed by distilling off the alcohol solvent, or according to a process comprising (5) allowing 1.01 to 1.15 moles of a quaternary phosphonium salt to react with one mole of ¼ alkali metal salt of bisphenol AF in alcohol, followed by distilling off the alcohol solvent.

DETAILED DESCRIPTION OF THE INVENTION

The alkali metal salt to be used in the foregoing reaction (1), (2) or (5) can be prepared by allowing one mole, 2 moles or ¼ moles of an alkali metal alkoxide, respectively, to react with one mole of bisphenol AF in alcohol at a temperature ranging from room temperature to about 50° C. The alkali metal alkoxide for use for the reaction includes, for example, sodium methoxide, potassium methoxide, etc., and the alcohol for use as a solvent in the reaction is, in general, methanol. Other alkali metal salts as lithium salt, cesium salt, rubidium salt, etc. can be used. The salts can be also formed from the corresponding alkali metal hydroxides.

In case of reaction (1) or (2), monoalkali metal salt or dialkali metal salt of bisphenol AF can be provided in an alcohol solution and then admixed with a quaternary phosphonium salt also provided in an alcohol solution in a molar ratio of the quaternary phosphonium salt to the alkali metal salt of 1.01–1.15:1 or 2.02–2.30:1, respectively.

In case of reaction (3), at first one mole of the alkali metal alkoxide is allowed to react with 1.01 to 1.15 moles of the quaternary phosphonium salt, followed by reaction with one mole of bisphenol AF.

In case of reaction (4), reaction of the same three reactants in the same molar ratios as in reaction (3) is carried out in an alcohol at the same time.

In case of reaction (5), ¼ alkali metal salt is used in place of the monoalkali metal salt of bisphenol used in reaction (1).

The quaternary phosphonium salt for use in the reaction includes, for example, tetraphenylphosphonium chloride, triphenylbenzylphosphonium chloride, triphenylbenzylphosphonium bromide, 3,4-dichlorobenzyl-triphenylphosphonium chloride, 1-(propa-2-on-yl)-triphenylphosphonium chloride, (ethoxycarbonylmethyl) triphenylphosphonium chloride, allyltriphenylphosphonium chloride, allyltriphenylphosphonium bromide, tetramethylphosphoniurm chloride, tetramethylphosphoniurm bromide, tetraethylphosphonium chloride, tetraethylphosphonium bromide, etc., among which triphenylbenzylphosphonium salts are preferable.

The quaternary phosphonium salt is allowed at first to react with bisphenol AF [2,2-bis(4-hydroxyphenyl) hexafluoropropane] in the presence of an alkali metal in a molar ratio of the quaternary phosphonium salt to the bisphenol AF of 1.01–1.15:1, preferably 1.02–1.10:1. Below a molar ratio of 1.01:1, e.g. at an equimolar ratio, the object of the present invention, e.g. improved vulcanization characteristics cannot be attained, whereas above 1.15:1, the hardness and compression set of the vulcanization products tend to increase, resulting in deterioration of the normal state physical properties.

To the reaction mixtures in the alcohol solvent obtained according to the processes (1), (3) and (4) is further added 2 to 4 moles, preferably 3 moles, of bisphenol A per mole of the bisphenol AF used for the formation of the reaction mixtures or to the reaction mixture in the alcohol solvent obtained according to the process (2) is added 3 to 7 moles, preferably 5 moles, of bisphenol AF per mole of the bisphenol AF used for the formation of the reaction mixture, followed by distilling off the alcohol solvent. In these cases, it is necessary to add the further bisphenol AF to the reaction mixtures in the alcohol solvent. In other words, when the further bisphenol AF is added to the reaction mixture as isolated from the alcohol solvent, followed by melting and mixing, no improvement of the vulcanization characteristics can be attained, as shown in Comparative Example 3, which follows. When the amount of the further bisphenol AF is below 2 moles for processes (1), (3) and (4) or below 3 moles for process (2), the compression set will be deteriorated, whereas above 4 moles for processes (1), (3) and (4) or above 7 moles for process (2), the vulcanization speed will be retarded.

In the process (5), it can be said that 4 moles of bisphenol AF is used on the basis of 1.01 to 1.15 moles of the quaternary phosphonium salt.

The products obtained by distilling off the alcohol solvent show a hygroscopic property and thus must be preserved in a tightly closed container just before used as a vulcanization promoter in the vulcanization of fluorine-containing elastomers.

Fluorine-containing elastomers for use in the vulcanization are preferably copolymers of vinylidene fluoride with at least one of other fluorinated olefin such as tetrafluoroethylene, hexafluoropropene, chlorotrifluoroethylene, trifluoroethylene, pentafluoropropene, vinyl fluoride, perfluoro(methyl vinyl ether), perfluoro(propyl vinyl ether), etc., particularly preferable copolymers include, for example, a binary copolymer of vinylidene fluoride-hexafluoropropene and a ternary copolymer of vinylidene fluoride-tetrafluoroethylene-hexafluoropropene.

About 0.1 to about 10 parts by weight, preferably about 0.5 to about 5 parts by weight, of the vulcanization promoter can be added to 100 parts by weight of the fluorine—containing elastomers. Furthermore, about 1 to about 15 parts by weight, preferably about 2 to about 6 parts by weight, of an oxide or hydroxide of a divalent metal such as magnesium, calcium, lead, zinc, etc. can be added as an acid acceptor to 100 parts by weight of the fluorine-containing elastomers.

The foregoing fluorine-containing elastomers, vulcanization promoter and acid acceptor can be kneaded, together with a filler or a reinforcing agent such as carbon black, silica, etc. and other necessary additives, through an open roll, Banbury mixer, etc., and the resulting kneaded product is then subjected to press vulcanization at about 1500 to about 200° C. for about 3 to about 30 minutes and then to oven vulcanization (secondary vulcanization) at about 200° to about 230° C. For about 20 to about 24 hours.

The present vulcanization promoter for fluorine-containing elastomers gives much more improved vulcanization characteristics such as vulcanization speed, while maintaining advantageous properties such as distinguished normal state physical properties, etc. as observed in case of vulcanization promoters of bisphenol AF quaternary phosphonium salt series.

PREFERRED EMBODIMENTS OF THE INVENTION

The present invention will be explained below, referring to Examples.

EXAMPLE 1

16.80 g (50 m moles) of bisphenol AF (BAF) and about 15 g of methanol were charged into a reactor vessel having a capacity of 500 ml with stirring at 50° C. to obtain a solution. Then, 2.70 g (50 m moles) of sodium methoxide was added to the solution, followed by stirring for 15 minutes to form a solution containing monosodium salt of bisphenol AF. Then, a solution containing 20.20 g (52 m moles) of benzyltriphenylphosphonium chloride (BTPPC) in about 15 g of methanol was added thereto, followed by stirring for 15 minutes to obtain a solution A containing a reaction mixture of one mole of BAF with 1.04 moles of BTPPC in methanol [BAF-1.04 BTPP]/MeOH].

A solution containing 50.40 g (150 m moles) of BAF in about 45 g of methanol was added to the methanol solution A, followed by stirring for 15 minutes to obtain a methanol solution B containing a reaction mixture of 4 moles of BAF with 1.04 moles of BTPPC ([4BAF-1.04 BTPP]/MeOH).

The resulting methanol solution B was concentrated in an evaporator to about 30% residues, and the resulting concentrate was slowly dropwise added to 4 L of water with stirring over 60 minutes to remove the byproduct NaCl and crystallize and precipitate the reaction mixture, followed by water washing, separation (decantation or filtration) and drying (at 40° C. in a vacuum drier for 20 hours or more).

The thus obtained vulcanization promoter (melting point: 58° C.) was preserved in a tightly closed container.

EXAMPLE 2

35.18 g of [BAF-1.04 BTPP] (corresponding to a mixture of 50 m moles of the reaction mixture with 2 m moles of unreacted BTPPC) obtained from methanol solution A of Example 1 ([BAF-1.04 BTPP]/MeOH) by application of the same concentration to dry steps as used for the methanol solution B of Example 1 and 30 g of methanol were charged into a reactor vessel having a capacity of 500 ml, followed by stirring at 50° C. to obtain a solution. Then, a solution containing 50.40 g (150 m moles) of BAF in about 45 g of methanol was added to the resulting solution, followed by stirring for 15 minutes to obtain a methanol solution containing a reaction mixture of 4 moles of BAF with 1.04 moles of BTPPC ([4BAF-1.04 BTPP]/MeOH).

Then, the methanol solution was subjected to the same concentration, crystallization and precipitation, water washing, separation and drying as in Example 1, and the resulting vulcanization promoter (melting point: 58° C.) was preserved in a tightly closed container.

EXAMPLE 3

16.80 g (50 m moles) of BAF and about 15 g of methanol were charged into a reactor vessel having a capacity of 500 ml, followed by stirring at 50° C. to obtain a solution. 5.40 g (100 m moles) of sodium methoxide was added to the solution, followed by stirring for 15 minutes to form a solution containing disodium salt of bisphenol AF. Then, a solution containing 40.40 g (104 m moles) of BTPPC in about 30 g of methanol was added to the resulting solution, followed by stirring for 15 minutes to obtain a methanol solution containing a reaction mixture of 1 mole of BAF with 2.08 moles of BTPPC ([BAF-2.08 BTPP]/MeOH).

A solution containing 117.60 g (350 m moles) of BAF in about 105 g of methanol was added to the resulting methanol solution, followed by stirring for 15 minutes to obtain a methanol solution containing a reaction mixture of 4 moles of BAF with 1.04 moles of BTPPC ([4BAF-1.04 BTPP]/MeOH).

Then, the methanol solution was subjected to the same concentration, crystallization and precipitation, water washing, separation and drying as in Example 1, and the resulting vulcanization promoter (melting point: 58° C.) was preserved in a tightly closed container.

EXAMPLE 4

In Example 1, the sequence of charging the methanol solution of BAF and the methanol solution of BTPPC to be used for the formation of methanol solution A was reversed. The resulting vulcanization promoter (melting point: 58° C.) was preserved in a tightly closed container.

EXAMPLE 5

67.20 g (200 m moles) and about 60 g of methanol were charged into a reactor vessel having a capacity of 500 ml with stirring at 50° C. to obtain a solution. 2.70 g (50 m moles) of sodium methoxide was added to the solution to form ¼ sodium salt of bisphenol AF. Then, a solution containing 20.20 g (52 m moles) of BTPPC in about 15 g of methanol was added to the resulting solution, followed by stirring for 15 minutes to obtain a methanol solution containing a reaction mixture of 4 moles of BAF with 1.04 moles of BTPPC ([4BAF-1.04 BTPP]/MeOH).

Then, the methanol solution was subjected to the same concentration, crystallization and precipitation, water washing separation and drying as in Example 1, and the resulting vulcanization promoter (melting point: 58° C.) was preserved in a tightly closed container.

EXAMPLE 6

16.80 g (50 m moles) of BAF, 20.20 g (52 m moles) of BTPPC and about 45 g of methanol were charged into a reactor vessel having a capacity of 500 ml with stirring at 50° C. to obtain a solution. Then, 2.70 g (50 m moles) of sodium methoxide was added to the solution, followed by stirring for 15 minutes to obtain a methanol solution containing a reaction mixture of 1 mole of BAF with 1.04 moles of BTPPC ([BAF-1.04 BTPP]/MeOH).

A solution containing 50.40 g (150 m moles) of BAF in about 45 g of methanol was added to the methanol solution, followed by stirring for 15 minutes to obtain a methanol solution containing a reaction mixture of 4 moles of BAF with 1.04 moles of BTPPC ([4BAF-1.04 BTPP]/MeOH).

Then, the resulting methanol solution was subjected the same concentration, crystallization and precipitation, water washing, separation and drying as in Example 1, and the resulting vulcanization promoter (melting point: 60° C.) was preserved in a tightly closed container.

EXAMPLE 7

16.80 g (50 m moles) of BAF and about 15 g of methanol were charged into a reactor vessel having a capacity of 500 ml, and then 2.80 g (50 m moles) of potassium methoxide was added thereto, followed by stirring at 50° C. for 15 minutes to form a solution containing a monopatassium salt of bisphenol AF. Then, a solution containing 20.20 g (52 m moles) of BTPPC in about 30 g of methanol was added thereto, followed by stirring for 15 minutes to obtain a methanol solution containing a reaction mixture of 1 mole of BAF with 1.04 moles of BTPPC ([BAF-1.04 BTPP]/MeOH).

A solution containing 50.40 g (150 m moles) of BAF in about 45 g of methanol was added to the methanol solution, followed by stirring for 15 minutes to obtain a methanol solution containing a reaction mixture of 4 moles of BAF with 1.04 moles of BTPPC ([4BAF-1.04 BTPP]) /MeOH).

Then, the resulting methanol solution was subjected to the same concentration, crystallization and precipitation, water washing separation and drying as in Example 1, and the resulting vulcanization promoter (melting point: 60° C.) was preserved in a tightly closed container.

EXAMPLES 8 TO 14

100 parts by weight of fluorine-containing elastomer comprising a ternary copolymer of vinylidene fluoride-tetrafluoroethylene-hexafluoropropene, 25 parts by weight of MT carbon black, 6 parts by weight of calcium hydroxide, 3 parts by weight of magnesium oxide and 2 parts by weight of one of vulcanization promoters (4BAF-1.04 BTPP) obtained in Examples 1 to 7 were kneaded through an open roll, and the resulting vulcanization products were each subjected to press vulcanization at 180° C. for 10 minutes and then to oven vulcanization (secondary vulcanization) at 230° C. for 22 hours.

These kneading products and vulcanization products were tested for the following items:

Vulcanization speed: Measurements of Tc10 (10% vulcanization time scorch time), Tc 90(90% vulcanization time: optimum vulcanization time), ML (minimum torque) and MH (maximum torque) by an oscillating disk rheometer Normal state physical properties: according to DIN 53505 and 53504

Compression set: according to DIN 53505 and 53504

Test results for Examples 8 to 14 are shown in the following Table 1:

TABLE 1

| Item | | Example No. | | | | | | |
|---|---|---|---|---|---|---|---|---|
| | | 8 | 9 | 10 | 11 | 12 | 13 | 14 |
| [Vulcanization speed] | | | | | | | | |
| Tc10 | (min.) | 2.40 | 2.40 | 2.40 | 2.40 | 2.40 | 2.40 | 2.40 |
| Tc90 | (min.) | 3.50 | 3.50 | 3.50 | 3.50 | 3.50 | 3.60 | 3.60 |
| ML | (Kg · cm) | 15.0 | 15.0 | 15.0 | 15.0 | 15.0 | 15.0 | 15.0 |
| MH | (Kg · cm) | 50.0 | 50.0 | 50.0 | 50.0 | 50.0 | 51.0 | 51.0 |
| [Normal state physical properties] | | | | | | | | |
| Hardness | | 66 | 66 | 66 | 66 | 66 | 66 | 67 |
| 100% Modulus | (MPa) | 4.0 | 4.0 | 4.0 | 4.0 | 4.0 | 4.0 | 3.8 |
| Tensile strength (stress at break) | (MPa) | 17 | 17 | 17 | 17 | 17 | 17 | 18 |
| Elongation (elongation at break) | (%) | 270 | 270 | 270 | 270 | 270 | 270 | 260 |
| [Compression set] | | | | | | | | |
| 200° C., 70 hr. | (%) | 20 | 20 | 20 | 20 | 20 | 20 | 21 |

EXAMPLES 15 TO 18 AND COMPARATIVE EXAMPLE 1

In Example 8, the following reaction mixtures of various molar ratios prepared in the same manner as in Example 1 were used as vulcanization promoters in the same amount in place of the vulcanization promoter obtained in Example 1:

4BAF-1.02BTPP (melting point: 58° C.) for Example 15
4BAF-1.04BTPP (melting point: 58° C.) for Example 16
4BAF-1.07BTPP (melting point: 58° C.) for Example 17
4BAF-1.10BTPP (melting point: 58° C.) for Example 18
4BAF-1.00BTPP (melting point: 60° C.) for Comparative Example 1

COMPARATIVE EXAMPLE 2

In Example 8, 4 moles of BAF and 1 mole of BTPPC as mixed at the kneading were used as a vulcanization promoter (melting point 120° C.) in the same amount in place of the vulcanization promoter obtained in Example 1.

COMPARATIVE EXAMPLE 3

In Example 8, [BAF-1.04 BTPP] obtained in the same manner as Example 2 as mixed with a 3-fold molar amount of BAF at the kneading was used as a vulcanization promoter (melting point:120° C.) in the same amount in place of the vulcanization promoter obtained in Example 1.

Test results of Examples 15 to 18 and Comparative Examples 1 to 3 are shown in the following Table 2:

TABLE 2

| Item | | Example No. | | | | Comp. Ex. No. | | |
|---|---|---|---|---|---|---|---|---|
| | | 15 | 16 | 17 | 18 | 1 | 2 | 3 |
| [Vulcanization speed] | | | | | | | | |
| Tc10 | (min.) | 2.50 | 2.40 | 2.20 | 1.90 | 3.00 | 4.20 | 3.80 |
| Tc90 | (min.) | 3.60 | 3.50 | 3.10 | 2.70 | 5.00 | 6.20 | 5.70 |
| ML | (Kg · cm) | 15.0 | 15.0 | 15.0 | 15.0 | 15.0 | 15.0 | 15.0 |
| MH | (Kg · cm) | 50.0 | 50.0 | 51.0 | 51.0 | 50.0 | 51.0 | 51.0 |
| [Normal state physical properties] | | | | | | | | |
| Hardness | | 66 | 66 | 67 | 68 | 66 | 66 | 66 |
| 100% Modulus | (MPa) | 4.0 | 4.0 | 4.1 | 4.2 | 3.9 | 3.8 | 3.8 |
| Tensile strength (stress at break) | (MPa) | 17 | 17 | 18 | 18 | 17 | 15 | 15 |
| Elongation (elongation at break) | (%) | 270 | 270 | 260 | 260 | 270 | 240 | 240 |
| [Compression set] | | | | | | | | |
| 200° C., 70 hr. | (%) | 20 | 20 | 21 | 21 | 20 | 23 | 23 |

What is claimed is:

1. A process for preparing a vulcanization promoter for fluorine-containing elastomers, which comprises allowing 1.01 to 1.15 moles of a quaternary phosphonium salt to react with one mole of a monoalkali metal salt of bisphenol AF in alcohol and then further adding additional bisphenol AF thereto, followed by distilling off the alcohol solvent.

2. A process according to claim 1, wherein the additional bisphenol AF further added is in an amount of 2 to 4 moles.

3. A process for preparing a vulcanization promoter for fluorine-containing elastomer, which comprises allowing 2.02 to 2.30 moles of a quaternary phosphonium salt to react with one mole of dialkali metal salt of bisphenol AF in alcohol and then further adding additional bisphenol thereto, followed by distilling off the alcohol solvent.

4. A process according to claim 3, wherein the additional bisphenol AF further added is in an amount of 3 to 7 moles.

5. A process for preparing a vulcanization promoter for fluorine-containing elastomers, which comprises allowing one mole each of an alkali metal alkoxide and bisphenol AF successively to react with 1.01 to 1.15 moles of a quaternary phosphonium salt in alcohol and then further adding additional bisphenol AF thereto, followed by distilling off the alcohol solvent.

6. A process according to claim 5, wherein the additional bisphenol AF further added is in an amount of 2 to 4 moles.

7. A process for preparing a vulcanization promoter for fluorine-containing elastomers, which comprises subjecting one mole of bisphenol AF, 1.01 to 1.15 moles of a quaternary phosphonium salt and one mole of an alkali metal alkoxide to reaction in alcohol and then further adding additional bisphenol AF thereto, followed by distilling off the alcohol solvent.

8. A process according to claim 7, wherein the additional bisphenol AF further added is in an amount of 2 to 4 moles.

9. A process for preparing a vulcanization promoter for fluorine-containing elastomers, which comprises allowing 1.01 to 1.15 moles of a quaternary phosphonium salt to react with one mole of ¼ alkali metal salt of bisphenol AF in alcohol, followed by distilling off the alcohol solvent.

* * * * *

UNITED STATES PATENT AND TRADEMARK OFFICE
CERTIFICATE OF CORRECTION

PATENT NO.   : 5,981,423
DATED        : January 12, 2000
INVENTOR(S)  : Hiroshi Kawasaki et al.

It is certified that error appears in the above-identified patent and that said Letters Patent is hereby corrected as shown below:

| Item | | 8 | 9 | 10 | 11 | 12 | 13 | 14 |
|---|---|---|---|---|---|---|---|---|
| [Vulcanization speed] | | | | | | | | |
| Tc10 | (min.) | 2.40 | 2.40 | 2.40 | 2.40 | 2.40 | 2.40 | 2.40 |
| Tc90 | (min.) | 3.50 | 3.50 | 3.50 | 3.50 | 3.50 | 3.60 | 3.60 |
| ML | (Kg·cm) | 15.0 | 15.0 | 15.0 | 15.0 | 15.0 | 15.0 | 15.0 |
| MH | (Kg·cm) | 50.0 | 50.0 | 50.0 | 50.0 | 50.0 | 51.0 | 51.0 |
| [Normal state physical properties] | | | | | | | | |
| Hardness | | 66 | 66 | 66 | 66 | 66 | 66 | 67 |
| 100% Modulus | (MPa) | 4.0 | 4.0 | 4.0 | 4.0 | 4.0 | 4.0 | 3.8 |
| Tensile strength (stress at break) | (MPa) | 17 | 17 | 17 | 17 | 17 | 17 | 18 |
| Elongation (elongation at break) | (%) | 270 | 270 | 270 | 270 | 270 | 270 | 260 |
| [Compression set] | | | | | | | | |
| 200°C, 70 hr. | (%) | 20 | 20 | 20 | 20 | 20 | 20 | 21 |

Column header: Example No. (8, 9, 10, 11, 12, 13, 14)

UNITED STATES PATENT AND TRADEMARK OFFICE
CERTIFICATE OF CORRECTION

PATENT NO.   : 5,981,423
DATED        : January 12, 2000
INVENTOR(S)  : Hiroshi Kawasaki et al.

It is certified that error appears in the above-identified patent and that said Letters Patent is hereby corrected as shown below:

EXAMPLES 15 TO 18 AND COMPARATIVE EXAMPLE 1

In Example 8, the following reaction mixtures of various molar ratios prepared in the same manner as in Example 1 were used as vulcanization promoters in the same amount in place of the vulcanization promoter obtained in Example 1:

4BAF-1.02BTPP    (melting point : 58°C) for Example 15
    4BAF-1.04BTPP    (melting point : 58°C) for Example 16
    4BAF-1.07BTPP    (melting point : 58°C) for Example 17
    4BAF-1.10BTPP    (melting point : 58°C) for Example 18
    4BAF-1.00BTPP    (melting point : 60°C) for Comparative Example 1

COMPARATIVE EXAMPLE 2

In Example 8, 4 moles of BAF and 1 mole of BTPPC as mixed at the kneading were used as a vulcanization promoter (melting point 120°C) in the same amount in place of the vulcanization promoter obtained in Example 1.

COMPARATIVE EXAMPLE 3

In Example 8, [BAF-1.04 BTPP] obtained in the same manner as Example 2 as mixed with a 3-fold molar amount of BAF at the kneading was used as a vulcanizaition promoter (melting point:120°C) in the same amount in place of the vulcanization promoter obtained in Example 1.

Test results of Examples 15 to 18 and Comparative Examples 1 to 3 are shown in the following Table 2:

UNITED STATES PATENT AND TRADEMARK OFFICE
CERTIFICATE OF CORRECTION

PATENT NO. : 5,981,423
DATED : January 12, 2000
INVENTOR(S) : Hiroshi Kawasaki et al.

It is certified that error appears in the above-identified patent and that said Letters Patent is hereby corrected as shown below:

| Item | | Example No. 15 | 16 | 17 | 18 | Comp. Ex. No. 1 | 2 | 3 |
|---|---|---|---|---|---|---|---|---|
| [Vulcanization speed] | | | | | | | | |
| Tc10 | (min.) | 2.50 | 2.40 | 2.20 | 1.90 | 3.00 | 4.20 | 3.80 |
| Tc90 | (min.) | 3.60 | 3.50 | 3.10 | 2.70 | 5.00 | 6.20 | 5.70 |
| ML | (Kg·cm) | 15.0 | 15.0 | 15.0 | 15.0 | 15.0 | 15.0 | 15.0 |
| MH | (Kg·cm) | 50.0 | 50.0 | 51.0 | 51.0 | 50.0 | 51.0 | 51.0 |
| [Normal state physical properties] | | | | | | | | |
| Hardness | | 66 | 66 | 67 | 68 | 66 | 66 | 66 |
| 100% Modulus | (MPa) | 4.0 | 4.0 | 4.1 | 4.2 | 3.9 | 3.8 | 3.8 |
| Tensile strength (stress at break) | (MPa) | 17 | 17 | 18 | 18 | 17 | 15 | 15 |
| Elongation (elongation at break) | (%) | 270 | 270 | 260 | 260 | 270 | 240 | 240 |
| [Compression set] | | | | | | | | |
| 200°C, 70 hr. | (%) | 20 | 20 | 21 | 21 | 20 | 23 | 23 |

Signed and Sealed this

Twenty-fifth Day of December, 2001

JAMES E. ROGAN
Director of the United States Patent and Trademark Office

*Attest:*

*Attesting Officer*